United States Patent
Hansen et al.

(10) Patent No.: US 12,394,095 B2
(45) Date of Patent: Aug. 19, 2025

(54) ONLINE STEREO CALIBRATION

(71) Applicant: Cilag GmbH International, Zug (CH)

(72) Inventors: Steen M. Hansen, Holte (DK); Mathias B. Stokholm, Soborg (DK); Johan M.V. Bruun, Hellerup (DK); Job Van Dieten, Rodovre (DK); Marco D.F. Kristensen, San Francisco, CA (US)

(73) Assignee: Cilag GmbH International, Zug (CH)

( * ) Notice: Subject to any disclaimer, the term of this patent is extended or adjusted under 35 U.S.C. 154(b) by 457 days.

(21) Appl. No.: 17/733,350

(22) Filed: Apr. 29, 2022

(65) Prior Publication Data

US 2023/0351636 A1 Nov. 2, 2023

(51) Int. Cl.
*G06T 7/80* (2017.01)
*A61B 34/10* (2016.01)
*A61B 34/20* (2016.01)
*A61B 90/00* (2016.01)

(52) U.S. Cl.
CPC ............. *G06T 7/85* (2017.01); *A61B 34/10* (2016.02); *A61B 34/20* (2016.02); *A61B 90/361* (2016.02); *A61B 2034/101* (2016.02); *A61B 2034/2068* (2016.02); *A61B 2090/367* (2016.02)

(58) Field of Classification Search
CPC ....... A61B 34/20; A61B 34/10; A61B 90/361; A61B 2034/101; A61B 2034/2068; G06T 7/70; G06T 7/85
See application file for complete search history.

(56) References Cited

U.S. PATENT DOCUMENTS

| | | |
|---|---|---|
| 9,274,046 B2 | 3/2016 | Stewart et al. |
| 11,033,182 B2 | 6/2021 | Hansen et al. |
| 11,039,734 B2 | 6/2021 | Hansen et al. |
| 2018/0263710 A1* | 9/2018 | Sakaguchi ............ A61B 90/14 |
| 2019/0117318 A1* | 4/2019 | Charron ............... A61B 5/0077 |
| 2020/0107886 A1* | 4/2020 | Govari .................... G06T 19/20 |
| 2021/0386503 A1* | 12/2021 | Healy .................... G16H 50/20 |

OTHER PUBLICATIONS

Maier-Hein, L., et al., "Optical techniques for 3D surface reconstruction in computer-assisted laparoscopic surgery," Medical Image Analysis, 2013, 17(8):974-996, 23 pgs.
Pratt, P., et al., "Practical Intraoperative Stereo Camera Calibration," Advances in Databases and Information Systems, Springer International Publishing, 2014, pp. 667-675, 9 pgs.
International Search Report and Written Opinion dated Aug. 11, 2023 for Application No. PCT/IB2023/054277, 11 pgs.

* cited by examiner

*Primary Examiner* — Margaret G Webb
(74) *Attorney, Agent, or Firm* — Frost Brown Todd LLP

(57) ABSTRACT

A stereo calibration system for minimally invasive surgery including a first image sensor configured to capture one or more first images of a patient anatomy and a second image sensor configured to capture one or more second images of a patient anatomy. The system further includes a processor configured to obtain calibration data associated with the first image sensor and the second image sensor, identify, based on a comparison of the one or more first images against the one or more second images, an offset, determine, based on the offset and the calibration data, whether the first image sensor or the second image sensor require re-calibration; and perform, based on the determination, at least one action.

20 Claims, 8 Drawing Sheets

ONLINE STEREO CALIBRATION

BACKGROUND

Surgical systems may incorporate an imaging system, which may allow the clinician(s) to view the surgical site and/or one or more portions thereof on one or more displays such as a monitor. The display(s) may be local and/or remote to a surgical theater. An imaging system may include a scope with a camera that views the surgical site and transmits the view to a display that is viewable by the clinician. Scopes include, but are not limited to, laparoscopes, robotic laparoscopes, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes.

Surgical imaging systems may also involve stereo vision, which can allow for 3D reconstruction of patient anatomy captured by the imaging systems. Scene reconstruction or 3D reconstruction is a process of capturing the shape and appearance of real objects. Thus, allowing medical professionals to use a scope-based imaging system to capture, reconstruct, and track an internal area of a patient as well as any tools present in the images.

While various kinds of surgical instruments and image captures systems have been made and used, it is believed that no one prior to the inventor(s) has made or used the invention described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
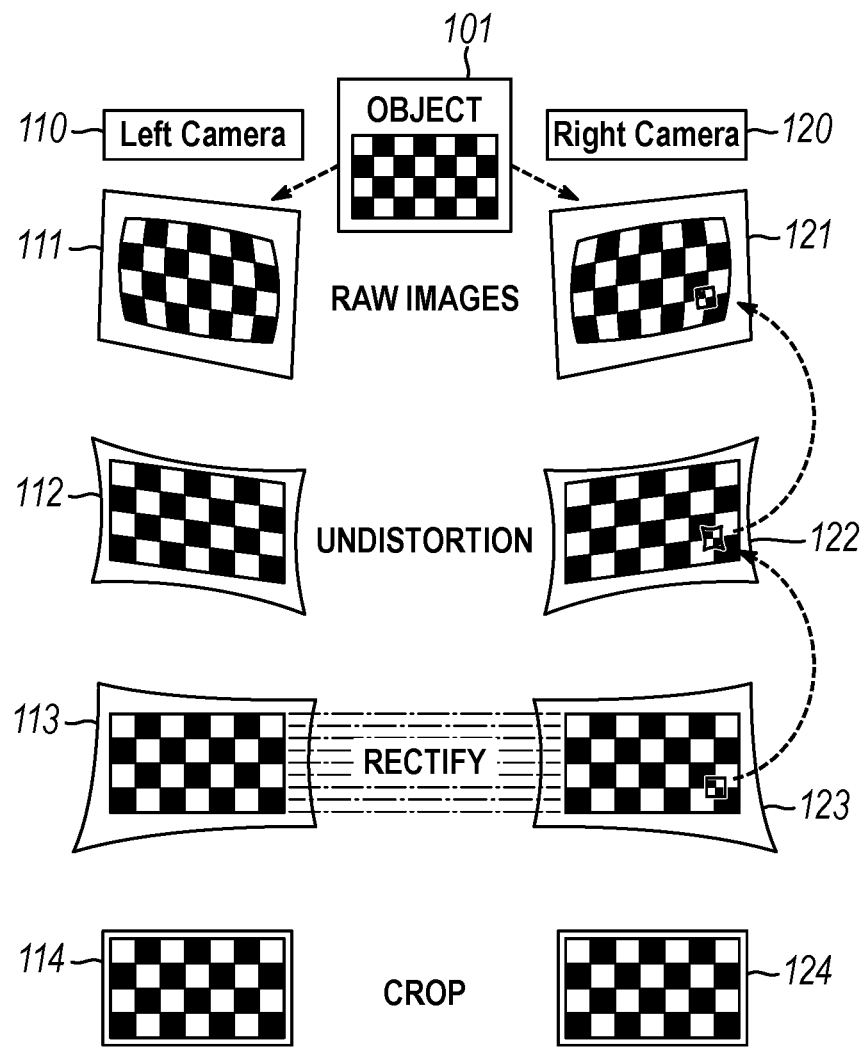
FIG. 1 depicts an illustrative flow diagram showing undistortion and rectification in a stereo image system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

Similarly, the phrase "based on" should be understood as referring to a relationship in which one thing is determined at least in part by what it is specified as being "based on." This includes, but is not limited to, relationships where one thing is exclusively determined by another, which relationships may be referred to using the phrase "exclusively based on."

I. CALIBRATION OF STEREO IMAGES IN COMPUTER VISION

FIG. 1 depicts an illustrative flow diagram showing the process of undistortion and rectification based on parameters that are determined during calibration in a stereo image system, such as disclosed herein. In some embodiments, and as shown, a single object 101 may be captured by two different (e.g., left 110 and right 120) image capture devices (e.g., cameras). As would be understood by one of ordinary skill in the art, capturing images of an object 101 from different locations and/or angles (e.g., from a left side 110 and a right side 120) relative to that object allows for stereo vision. As used herein, stereo vision means capturing at least two images that allow for computing of depth of field based on disparity between the images. As discussed herein, computing the depth of field and/or disparity may involve matching up features in the at least two images.

It should be understood that various calibration methods and/or images may be used. Thus, although FIG. 1 only shows using an image of a checkerboard pattern, it should be understood that other calibration images may be used as well. As shown in FIG. 1, a camera calibration method using the checkerboard pattern allows for high-precision calibration under complicated illumination. In general, calibration of stereo images in computer vision is well known in the art and should be understood by one of ordinary skill. In one example embodiment, the calibration involves a few general steps. First, the system may detect checkerboard corners, for example using an improved Harris corner detector. Regardless of algorithm, the system may try to find the specified number of checkerboard corners in each input image.

Next, the system may perform the optional step of estimating undistortion coefficients. For example, in some embodiments, the algorithm will solve for coefficients that minimize standard lens distortion. Although this does not undistort the original photographs or video, these coefficients can then be used in the calibration and reconstruction process to minimize error due to lens distortion. The system may also estimate a direct linear transformation. For example, the algorithm may estimate a set of optimized direct linear transformation coefficients that can be used to reconstruct points and curves from each view into 3D. Finally, the system may estimate calibration accuracy. In some embodiments, the algorithms may estimate the calibration, using a separate set of images within the calibration set (if a sufficient number of images are supplied).

In some embodiments, and as shown, raw images (e.g., 111 and 121) may be captured from the image capture devices. Due to the nature of surgical scopes and their operating conditions, the captured raw images (111 and 121) may be deformed by radial and tangential distortion, such as may be caused by the lenses of image capture devices. Accordingly, in some embodiments, the raw images may be transformed by the system, such as, for example, by removing distortion 112 and 122.

Typically, an image processing system creates a matrix that corresponds to each pixel in an image and through interpolation, the system can then remove distortion 112 and 122. Once the distortion is removed, the images may be morphed/deformed so that the image planes become coplanar and row-aligned and thus rectify the images 113 and 123. Once images have been rectified, the system may crop them 114 and 124 in such a way as to emphasize the common area between both images. In some embodiments, the calibration may also consider the alignment between the two stereo image capture devices. As part of the process of analyzing and correcting the raw images 111 and 121 (e.g., removing the distortion, rectifying, and cropping the image) a system can collect information associated with each step for future use. Stated differently, once the system has determined how to correct one set of captured images, it can correct future images captured by the same stereo image device using the collected metrics.

II. ONLINE/REAL-TIME STEREO CALIBRATION

Figure 3:
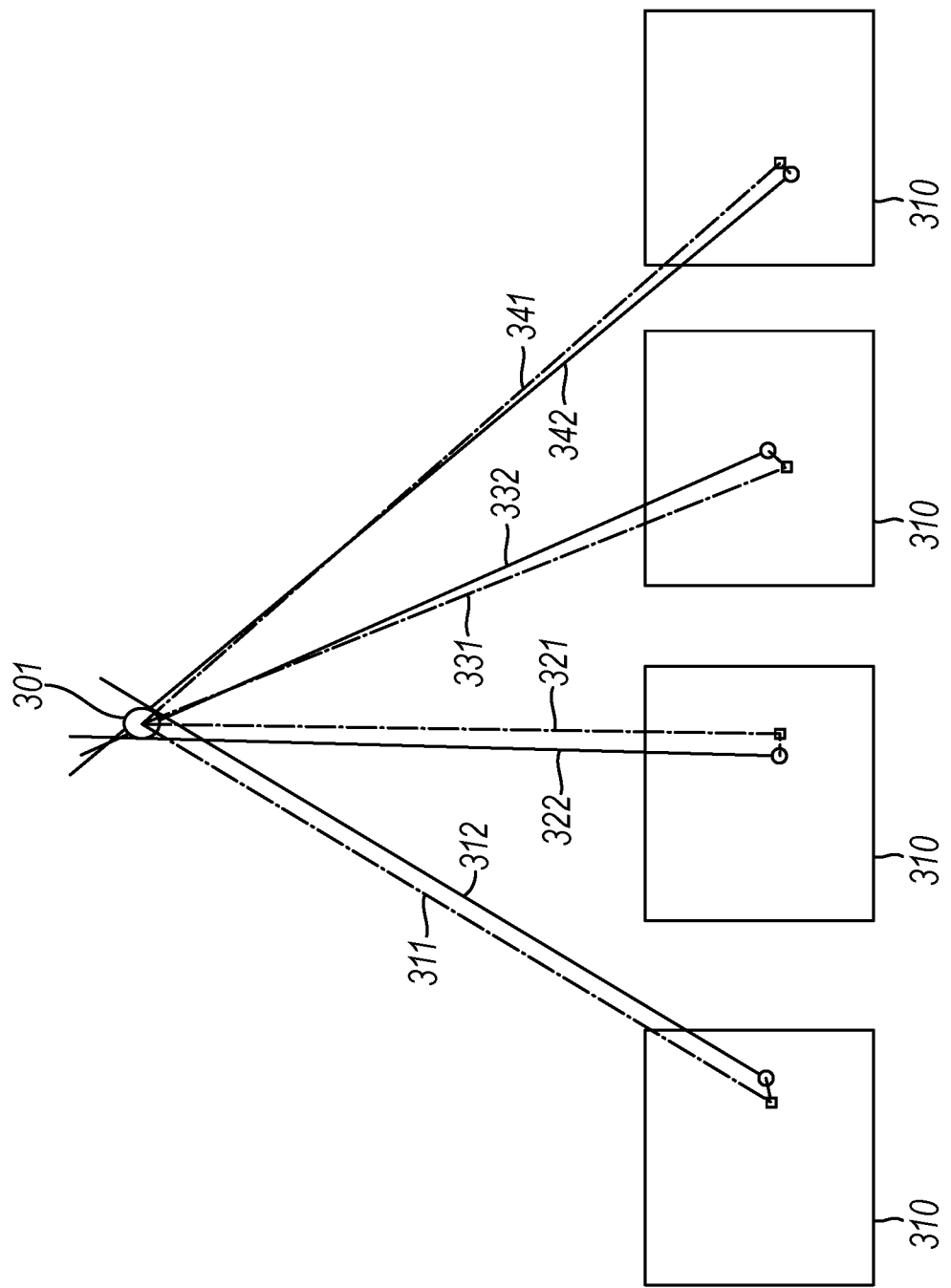
FIG. 3 illustrates error which may exist due to calibration drift, calibration error, or image localization error.

As discussed in the prior section, a system such as may be implemented based on this disclosure may obtain metrics associated with the stereo image device (e.g., initial calibration data) for use in deriving three dimensional information, such as triangulations of individual points or a three dimensional reconstruction of the scene as a whole, from subsequently captured images. However, in some cases, a system implemented based on this disclosure may not simply use initial calibration data, and instead may include features which address the possibility that a camera's characteristics may not remain constant after its initial calibration. For example, in the case of cameras used in the context of minimally invasive surgery, the accuracy of a stereo camera's calibration may be impacted by activities such as sterilization, or may drift during storage and/or transportation, or even during a procedure itself. An illustration of the types of errors this may introduce is shown in FIG. 3, as shown in that figure, a plurality of image capture devices 310, 320, 330, and 340 may be used to determine a computed 3D point 301. However, because the calibration of those devices may drift, the calibrated projection lines 311, 321, 331, 341 of point 301 may drift away from the actual point, as shown with lines 312, 322, 332 and 342. To account for this type of error, referred to as "reprojection error," some embodiments may provide for monitoring and/or updating of calibration during a procedure so that the accuracy of three dimensional reconstructions of the surgical site are not compromised by incorrect calibration.

Figure 2:
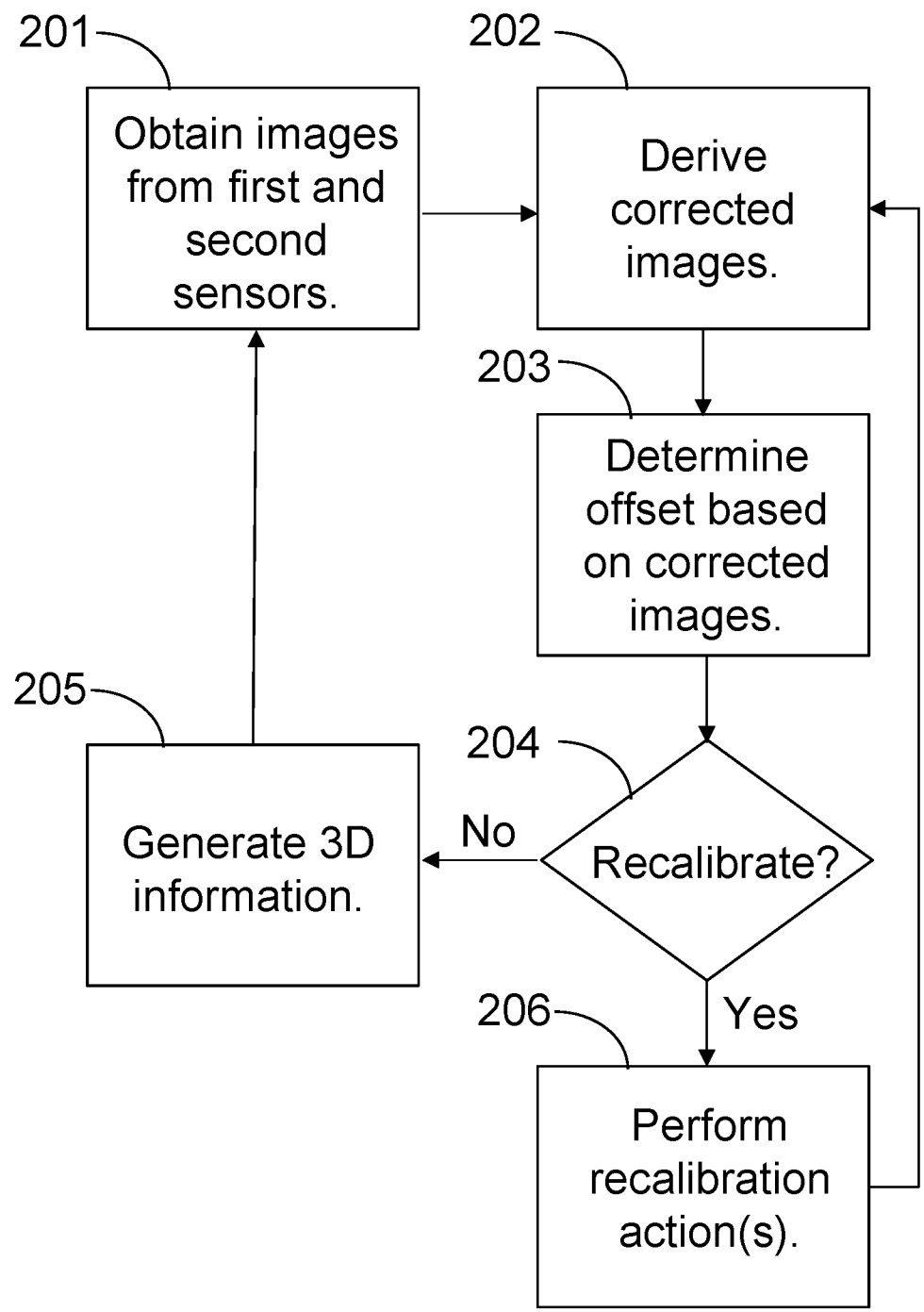
FIG. 2 depicts an illustrative flowchart of a method which could be performed by a surgical visualization system based on this disclosure.

Referring now to FIG. 2, that figure depicts an illustrative flowchart of a method which could be performed by a surgical visualization system based on this disclosure. In some embodiments, a system implemented based on this disclosure may obtain 201 images from first and second image sensors (e.g., left and right sensors from a stereo camera). These images may then be used to derive 202 corrected images (e.g., rectified images) using calibration data such as could be created in a process such as described above. This calibration data may include both intrinsic and extrinsic parameters/characteristics. Extrinsic parameters are parameters that identify the transformation between a camera reference frame, a world reference frame, and the relative transformation between the two cameras. Determining these parameters may involve determining a translation vector between the relative positions of the origins of the two reference frames and also determining the rotation matrix that brings the corresponding axes of the two frames into alignment. Intrinsic parameters generally characterize the optical, geometric, and digital characteristics of the camera, such as, for example, the perspective projection (i.e., focal length), the transformation between image plane coordinates and pixel coordinates, and the geometric distortion introduced by the optics.

Once the corrected images had been derived 202, those images may be used to determine 203 an offset which, as shown, could be used in a subsequent determination 204 of whether it would be appropriate to recalibrate the image sensors. Various non-limiting examples of how this type of offset determination 203 may be performed are described below in the context of FIGS. 4 and 5. Although the use of scanlines is primarily discussed herein, it should be understood that alternative embodiments may exist, such as, for example, using tool geometry to calculate offsets (discussed herein), and/or using a neural network AI to predict bad calibration.

Figure 4:
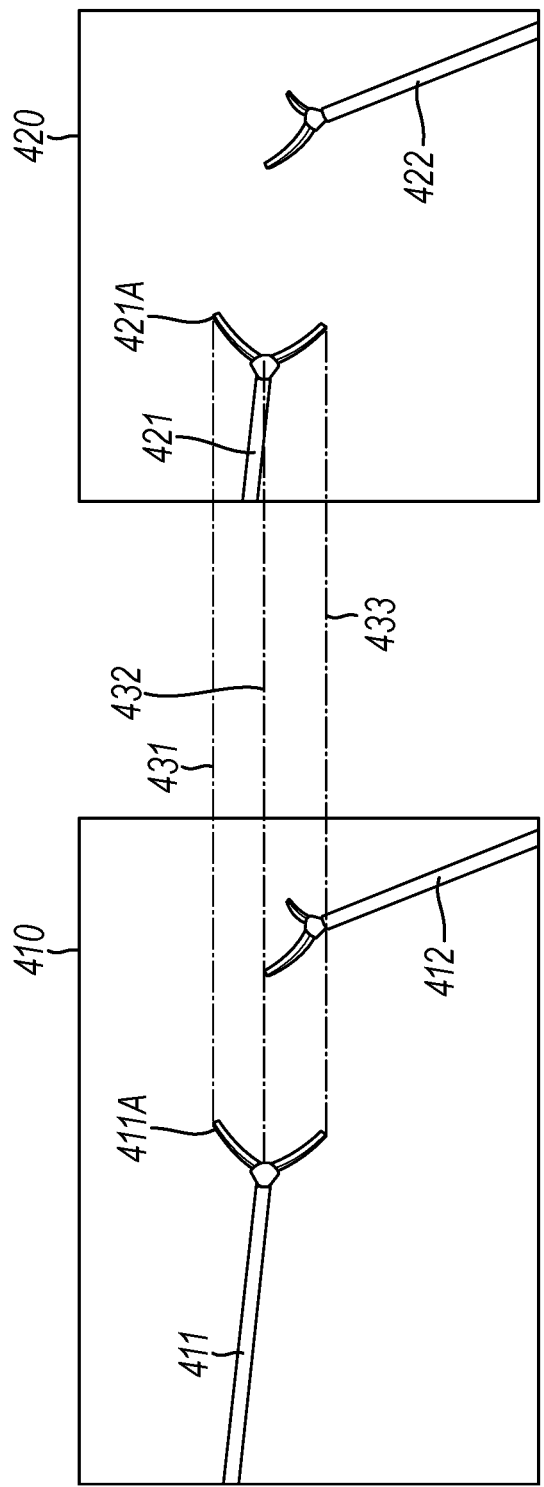
FIG. 4 depicts a pair of example corrected images such as could be derived from raw images captured by image sensors in a stereo imaging system.

Referring now to FIG. 4, a pair of example corrected images such as could be derived from images captured by image sensors in a stereo imaging system is shown. Specifically, FIG. 4 shows a first corrected image 410 derived (e.g., though the use of calibration data as described previously in the context of FIG. 1) from an image captured by a first image sensor (e.g., a left camera) and a second corrected image 420 derived from an image captured by a second image sensor (e.g., a right camera). In some embodiments, and as shown, the first corrected image 410 may contain a view of one or more tools 411 and 412 and the second corrected image 420 may contain an alternative view of the one or more tools 421 and 422. In minimally invasive surgery, surgeons are typically using laparoscopic tools to perform internal surgery. Thus, described herein, some embodiments of the disclosed technology the system may utilize the known 3D shapes of tools to determine if calibration is needed, and in some cases, carry out the calibration. Other embodiments may also exist, for example, carrying out an online calibration check and/or recalibration based on images that are not known (e.g., tools without known geometry, patient anatomy, etc.).

In some embodiments, a portion, or all, of one or more tools (e.g., the tip of a tool 411A and 421A) may be identified by the system. For example, the system may have been given a surgical plan that includes a listing of all possible tools, and their specific characteristics, which would be used during the procedure. In an alternative example, the system may have, or obtain, a database of surgical tools, including their specific characteristics. Stated differently, the system may know, prior to analyzing the images, what tools are expected to be present in the stereo images and what their specific characteristics should be. Specifically, the system may know or obtain the tool size, shape, color, construction material, and the like. In a further embodiment, the tool may have an identifying marker that the system can use to associate it with a known tool's characteristics. In an alternative embodiment, the system may use a deep-learning neural network that has been trained on various surgical tools to track and/or identify the tools.

Figure 5:
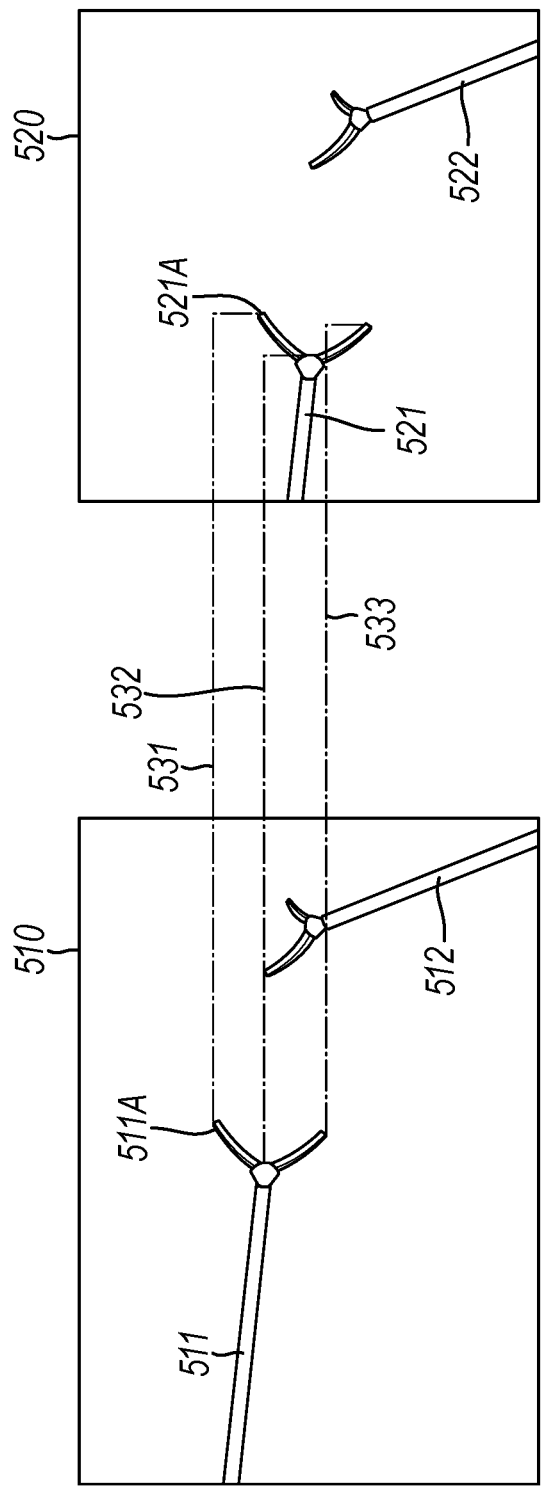
FIG. 5 depicts a scenario in which scan lines indicate the presence of an offset.

The tool locations, combined with the known information regarding their characteristics may then be used to identify features which can be used in determining 203 an offset. This may be done, for example, by evaluating scan lines from a feature of a tool (e.g., a distal tip) in a corrected image derived from an image captured with a first image sensor with that feature in a corresponding (e.g., derived from a simultaneously captured image) corrected image from a second image sensor. For example, if the image sensors are horizontally offset from each other, then alignment may be evaluated by determining if the corresponding features of a tool shown in corrected images derived from images captured by both first and second image sensors are vertically registered with each other, such as shown in FIG. 4. Thus, in a scenario corresponding to FIG. 4, a system implemented based on this disclosure may conclude that no calibration drift has occurred, or that the amount of calibration drift is negligible. However, in some cases, such as shown in FIG. 5, the scan lines 531, 532, and 533 may indicate the presence of an offset (e.g., a vertical offset as shown) between the first image 510 and the second image 520, indicating that at least some level of calibration drift has occurred. In some embodiments, other features/characteristics may also be compared. For example, a pivot point of a tool, a tip other than a distal tip, etc. may be used in determining an offset. As shown in FIG. 4, one or more scan lines (e.g., 431, 432, and 433) may be used to align the identified tool features/characteristics (e.g., 411A and 421A) of tool 411 and/or tool 412 in the first image 410 and of tool 421 and/or tool 422 in the second image 420.

Returning now to the discussion of FIG. 2, after an offset has been determined 203, a further determination 204 may be made as to whether it would be appropriate to recalibrate the stereo camera used to capture images. This may be done, for example, by determining if an offset indicated that there had been any drift from the initial calibration (e.g., if scan lines from a tool feature were not perfectly aligned between representations of a tool in images captured from first and second image sensors). However, other approaches are also possible. For example, in some cases, known dimensions of tools depicted in images from the first and second image sensors may be used to convert a pixel offset value into spatial measurements, such as millimeters, and these spatial measurement values may be compared against a threshold for the surgical procedure to determine 204 the appropriateness of recalibration. For instance, in a case where the disclosed technology is used during a procedure which does not require sub-millimeter accuracy (e.g., hernia reconstruction), if the offset was a millimeter or less, then the determination 204 may indicate that recalibration is not appropriate, even though there had been some drift from the calibration values then being used. Other variations, such as using thresholds based on pixel offset values rather than spatial measurement offset values, are also possible, and will be immediately apparent to those of ordinary skill in the art in light of this disclosure. Accordingly, the above description of how it may be determined 204 whether recalibration is appropriate should be understood as being illustrative only, and should not be treated as limiting.

Figure 6A:
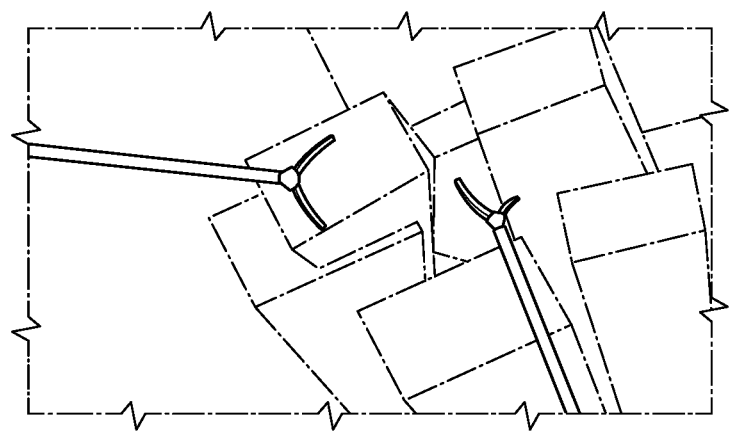
FIGS. 6A-6C depict geometry of tools which may be used in recalibration in some embodiments.
Figure 6B:
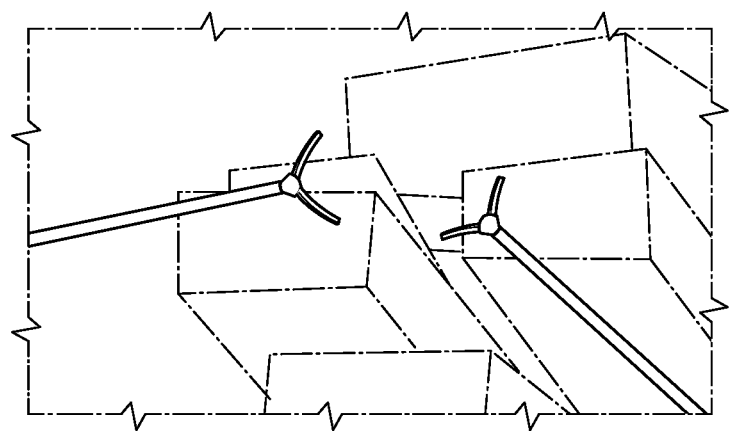
Figure 6C:
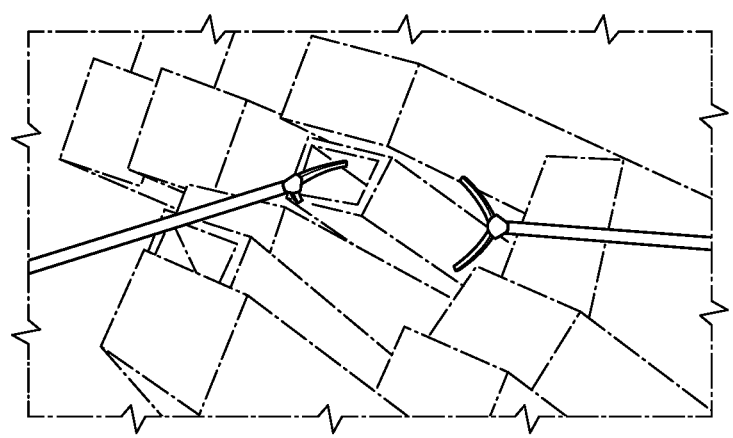

As shown in FIG. 2, if it was determined that there was no need for recalibration, then the previously derived 202 corrected images could be used to generate 205 3D information (e.g., a 3D reconstruction of the surgical site, triangulated locations in 3D of user specified points, tool tips or other points of interest), and the process could return to capture 201 further images. This could then be repeated throughout the surgical procedure. Alternatively, if it was determined 204 that recalibration was appropriate, then a method such as show in FIG. 2 could proceed with the performance 206 of at least one recalibration action. This may include, for example, requesting that a user of the system move one or more known tools in the field of view of a stereo camera, thereby allowing the system to capture images such as shown in FIGS. 6A, 6B and 6C in which the geometry of those tools could be used (instead of the checkerboard pattern) to recalibrate the camera in a manner such as described previously in the context of FIG. 1. Alternatively, in some cases, rather than requesting that the user move one or more known tools, a system performing a process such as shown in FIG. 2 may request that the user move the stereo camera to obtain images showing the relevant known tool from a variety of perspectives. As yet another variation, in some cases a system implemented based on this disclosure may be configured to store images from sensors of a stereo camera in a memory buffer as they are obtained 201, and could use images from the memory buffer in recalibrating the stereo camera, rather than requesting the user take some additional action to capture additional images. In any of the above cases though, after a stereo camera had been recalibrated, the calibration data used to derive 202 corrected images may be updated by being replaced with the new calibration data, and the process may continue through the use of that updated calibration data rather than the calibration data used to derive 202 the previous corrected images.

Other variations on potential implementations of the disclosed technology are also possible. For example, while FIGS. 4 and 5 depict evaluation of alignment based on vertical offsets, other offsets may be used, such as horizontal offsets in a case where image capture devices are vertically offset relative to each other. Similarly, while the example embodiments described herein are referenced as having two image sensors (e.g., left and right cameras making up a stereo image system), it should be understood that the system may have more than two image sensors. It should also be understood that, although the image sensors disclosed herein may be implemented as scope-based image sensors (e.g., image sensors used to capture images for a laparoscopic stereo camera), other types of image sensor may be used. Furthermore, calibration as described herein may take place outside as well as inside a patient.

As another possible type of variation, in some cases, rather than evaluating the need of/and or performing recalibrations based on characteristics of known tools, it may be possible perform those activities using other known objects in the surgical site. For example, in some embodiments, the system may obtain pre-operative information associated with the patient anatomy, such as, for example, pre-operative image data (e.g., magnetic resonance imaging (MRI), computed tomography (CT), Position emission tomography (PET/CT), ultrasound, radiography (x-ray), and the like). Thus, in some cases a system implemented based on this disclosure may use characteristics of known portions of patient anatomy, either instead of, or in addition to, known characteristics of known tools. Other variations are also possible, and will be immediately apparent to those of ordinary skill in light of this disclosure (e.g., performing online calibration using known objects in contexts other than surgical procedures). Alternatively, in some embodiments, functionality which was described above as being perform in the surgical site using characteristics of known tools may be performed externally. For example, in some cases if it was detected that recalibration was appropriate, a recalibration notice may be provided to a user requesting that he or she remove a stereo camera from the surgical site and take remedial actions, such as continuing the procedure with a different camera, or recalibrating the camera outside of the surgical site, such as through use of a convention calibration target such as shown in FIG. 1. Accordingly, the above description of how online calibration may be evaluated and/or performed in the context of a surgical procedure should be understood as being illustrative only, and should not be treated as limiting.

III. OVERVIEW OF EXEMPLARY SURGICAL VISUALIZATION SYSTEM

Figure 7:
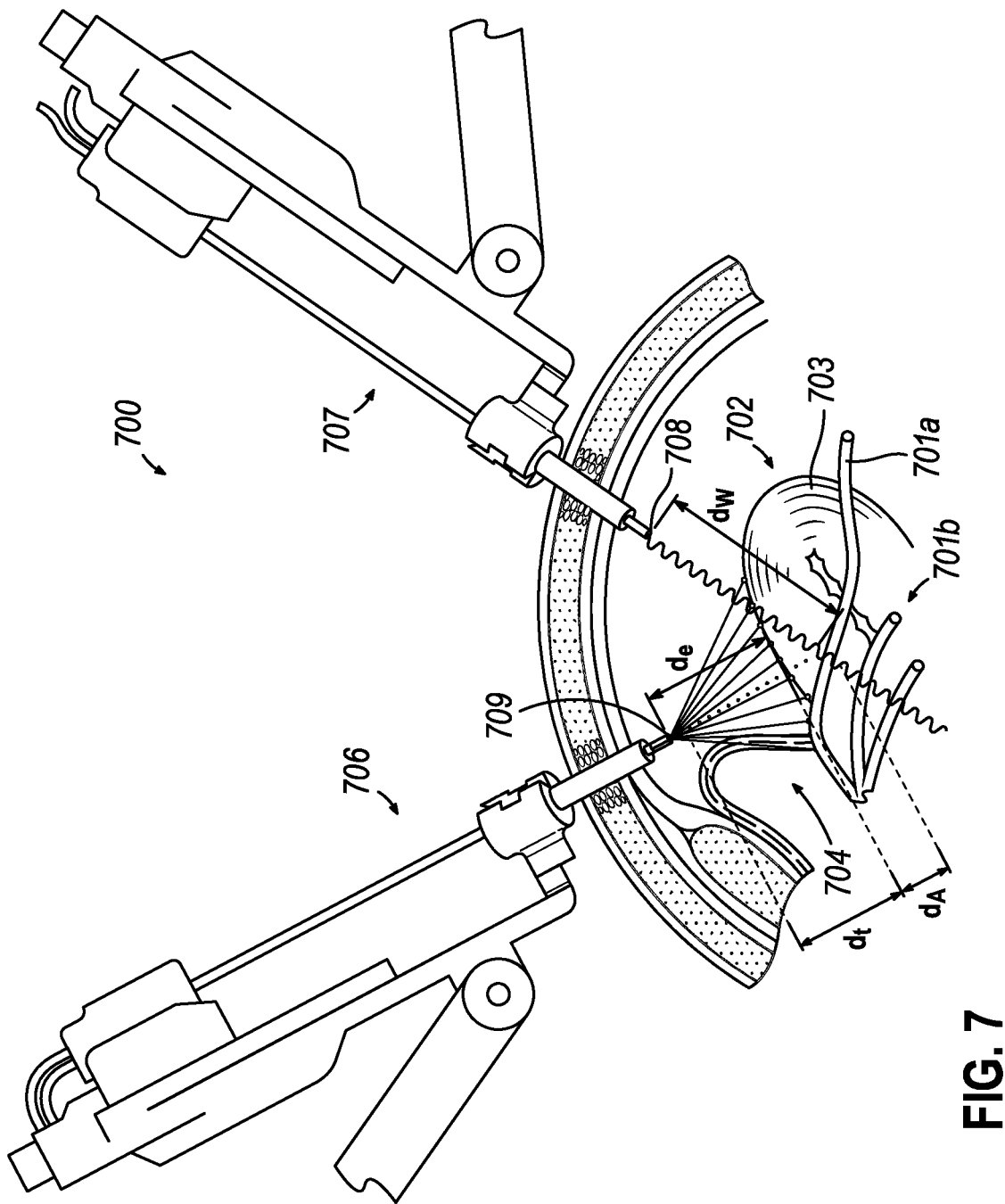
FIG. 7 depicts a schematic view of a surgical visualization system.

FIG. 7 depicts a schematic view of a surgical visualization system 700 according to at least one aspect of the present disclosure. The surgical visualization system 700 may create a visual representation of a critical structure 701a, 701b within an anatomical field. The surgical visualization system 700 may be used for clinical analysis and/or medical intervention, for example. In certain instances, the surgical visualization system 700 may be used intraoperatively to provide real-time, or near real-time, information to the clinician regarding proximity data, dimensions, and/or distances during a surgical procedure. The surgical visualization system 700 is configured for intraoperative identification of critical structure(s) and/or to facilitate the avoidance of critical structure(s) 701a, 701b by a surgical device. For example, by identifying critical structures 701a, 701b, a clinician may avoid maneuvering a surgical device into a critical structure 701a, 701b and/or a region in a predefined proximity of a critical structure 701a, 701b during a surgical procedure. The clinician may avoid dissection of and/or near a vein, artery, nerve, and/or vessel, for example, identified as a critical structure 701a, 701b, for example. In various instances, critical structure(s) 701a, 701b may be determined on a patient-by-patient and/or a procedure-by-procedure basis.

Critical structures 701a, 701b may be any anatomical structures of interest. For example, a critical structure 701a, 701b may be a ureter, an artery such as a superior mesenteric artery, a vein such as a portal vein, a nerve such as a phrenic nerve, and/or a sub-surface tumor or cyst, among other anatomical structures. In other instances, a critical structure 701a, 701b may be any foreign structure in the anatomical field, such as a surgical device, surgical fastener, clip, tack, bougie, band, and/or plate, for example. In one aspect, a critical structure 701a, 701b may be embedded in tissue. Stated differently, a critical structure 701a, 701b may be positioned below a surface of the tissue. In such instances, the tissue conceals the critical structure 701a, 701b from the clinician's view. A critical structure 701a, 701b may also be obscured from the view of an imaging device by the tissue. The tissue may be fat, connective tissue, adhesions, and/or organs, for example. In other instances, a critical structure 701a, 701b may be partially obscured from view. A surgical visualization system 700 is shown being utilized intraoperatively to identify and facilitate avoidance of certain critical structures, such as a ureter 701a and vessels 701b in an organ 702 (the uterus in this example), that are not visible on a surface 703 of the organ 702.

With continuing reference to FIG. 7, the surgical visualization system 700 incorporates tissue identification and geometric surface mapping, potentially in combination with a distance sensor system 704. In combination, these features of the surgical visualization system 700 may determine a position of a critical structure 701a, 701b within the anatomical field and/or the proximity of a surgical device 706 to the surface 703 of the visible tissue and/or to a critical structure 701a, 701b. The surgical device 706 may include an end effector having opposing jaws (not shown) and/or other structures extending from the distal end of the shaft of the surgical device 706. The surgical device 706 may be any suitable surgical device such as, for example, a dissector, a stapler, a grasper, a clip applier, a monopolar RF electrosurgical instrument, a bipolar RF electrosurgical instrument, and/or an ultrasonic instrument. As described herein, a surgical visualization system 700 may be configured to achieve identification of one or more critical structures 701a, 701b and/or the proximity of a surgical device 706 to critical structure(s) 701a, 701b.

The depicted surgical visualization system 700 includes an imaging system that includes an imaging device 707, such as a camera or a scope, for example, that is configured to provide real-time views of the surgical site. In various instances, an imaging device 707 includes a spectral camera (e.g., a hyperspectral camera, multispectral camera, a fluorescence detecting camera, or selective spectral camera), which is configured to detect reflected or emitted spectral waveforms and generate a spectral cube of images based on the molecular response to the different wavelengths. Views from the imaging device 707 may be provided to a clinician; and, in various aspects of the present disclosure, may be augmented with additional information based on the tissue identification, landscape mapping, and input from a distance sensor system 704. In such instances, a surgical visualization system 700 includes a plurality of subsystems—an imaging subsystem, a surface mapping subsystem, a tissue identification subsystem, and/or a distance determining subsystem. These subsystems may cooperate to intraoperatively provide advanced data synthesis and integrated information to the clinician(s).

The imaging device 707 of the present example includes an emitter 708, which is configured to emit spectral light in a plurality of wavelengths to obtain a spectral image of hidden structures, for example. The imaging device 707 may also include a three-dimensional camera and associated electronic processing circuits in various instances. In one aspect, the emitter 708 is an optical waveform emitter that is configured to emit electromagnetic radiation (e.g., near-infrared radiation (NIR) photons) that may penetrate the surface 703 of a tissue 702 and reach critical structure(s) 701a, 701b. The imaging device 707 and optical waveform emitter 708 thereon may be positionable by a robotic arm or a surgeon manually operating the imaging device. A corresponding waveform sensor (e.g., an image sensor, spectrometer, or vibrational sensor, etc.) on the imaging device 707 may be configured to detect the effect of the electromagnetic radiation received by the waveform sensor.

The wavelengths of the electromagnetic radiation emitted by the optical waveform emitter 708 may be configured to enable the identification of the type of anatomical and/or physical structure, such as critical structure(s) 701a, 701b. The identification of critical structure(s) 701a, 701b may be accomplished through spectral analysis, photo-acoustics, fluorescence detection, and/or ultrasound, for example. In one aspect, the wavelengths of the electromagnetic radiation may be variable. The waveform sensor and optical waveform emitter 708 may be inclusive of a multispectral imaging system and/or a selective spectral imaging system, for example. In other instances, the waveform sensor and optical waveform emitter 708 may be inclusive of a photoacoustic imaging system, for example. In other instances, an optical waveform emitter 708 may be positioned on a separate surgical device from the imaging device 707. By way of example only, the imaging device 707 may provide hyperspectral imaging in accordance with at least some of the teachings of U.S. Pat. No. 9,274,046, entitled "System and Method for Gross Anatomic Pathology Using Hyperspectral Imaging," issued Mar. 1, 2016, the disclosure of which is incorporated by reference herein in its entirety.

The depicted surgical visualization system 700 also includes an emitter 709, which is configured to emit a pattern of light, such as stripes, grid lines, and/or dots, to enable the determination of the topography or landscape of a surface 703. For example, projected light arrays may be used for three-dimensional scanning and registration on a surface 703. The projected light arrays may be emitted from an emitter 709 located on a surgical device 706 and/or an imaging device 707, for example. In one aspect, the projected light array is employed to determine the shape defined by the surface 703 of the tissue 702 and/or the motion of the surface 703 intraoperatively. An imaging device 707 is configured to detect the projected light arrays reflected from the surface 703 to determine the topography of the surface 703 and various distances with respect to the surface 703. By way of further example only, a visualization system 700 may utilize patterned light in accordance with at least some of the teachings of U.S. Pat. Pub. No. 2017/0055819, entitled "Set Comprising a Surgical Instrument," published Mar. 2, 2017, issued as U.S. Pat. No. 11,033,182 on Jun. 15, 2021, the disclosure of which is incorporated by reference herein in its entirety; and/or U.S. Pat. Pub. No. 2017/0251900, entitled "Depiction System," published Sep. 7, 2017, issued as U.S. Pat. No. 11,039,734 on Jun. 22, 2021, the disclosure of which is incorporated by reference herein in its entirety.

The depicted surgical visualization system 700 also includes a distance sensor system 704 configured to determine one or more distances at the surgical site. In one aspect, the distance sensor system 704 may include a time-of-flight distance sensor system that includes an emitter, such as the structured light emitter 709; and a receiver (not shown), which may be positioned on the surgical device 706. In other instances, the time-of-flight emitter may be separate from the structured light emitter. In one general aspect, the emitter portion of the time-of-flight distance sensor system 704 may include a laser source and the receiver portion of the time-of-flight distance sensor system 704 may include a matching sensor. A time-of-flight distance sensor system 704 may detect the "time of flight," or how long the laser light emitted by the structured light emitter 709 has taken to bounce back to the sensor portion of the receiver. Use of a very narrow light source in a structured light emitter 709 may enable a distance sensor system 704 to determine the distance to the surface 703 of the tissue 702 directly in front of the distance sensor system 704.

Referring still to FIG. 7, a distance sensor system 704 may be employed to determine an emitter-to-tissue distance ($d_e$) from a structured light emitter 709 to the surface 703 of the tissue 702. A device-to-tissue distance ($d_t$) from the distal end of the surgical device 706 to the surface 703 of the tissue 702 may be obtainable from the known position of the emitter 709 on the shaft of the surgical device 706 relative to the distal end of the surgical device 706. In other words, when the distance between the emitter 709 and the distal end of the surgical device 706 is known, the device-to-tissue distance ($d_t$) may be determined from the emitter-to-tissue distance ($d_e$). In certain instances, the shaft of a surgical device 706 may include one or more articulation joints; and may be articulatable with respect to the emitter 709 and the jaws. The articulation configuration may include a multi-joint vertebrae-like structure, for example. In certain instances, a three-dimensional camera may be utilized to triangulate one or more distances to the surface 703.

As described above, a surgical visualization system 700 may be configured to determine the emitter-to-tissue distance ($d_e$) from an emitter 709 on a surgical device 706 to the surface 703 of a uterus 702 via structured light. The surgical visualization system 700 is configured to extrapolate a device-to-tissue distance ($d_t$) from the surgical device 706 to the surface 703 of the uterus 702 based on emitter-to-tissue distance ($d_e$). The surgical visualization system 700 is also configured to determine a tissue-to-ureter distance ($d_A$) from a ureter 701a to the surface 703 and a camera-to-ureter distance ($d_w$), from the imaging device 707 to the ureter 701a. Surgical visualization system 700 may determine the camera-to-ureter distance ($d_w$), with spectral imaging and time-of-flight sensors, for example. In various instances, a surgical visualization system 700 may determine (e.g., triangulate) a tissue-to-ureter distance ($d_A$) (or depth) based on other distances and/or the surface mapping logic described herein.

Figure 8:
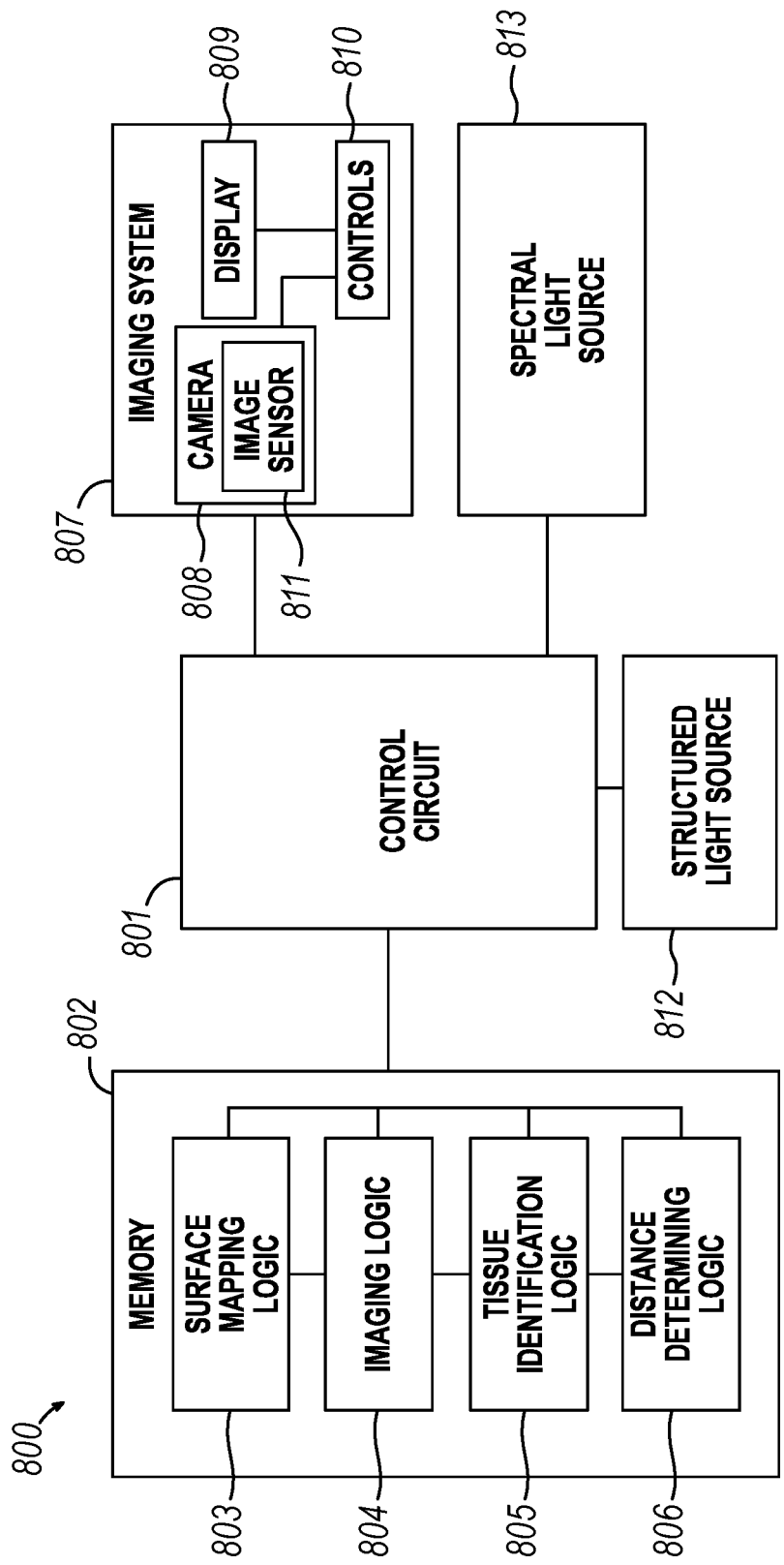
FIG. 8 depicts a schematic diagram of a control system.

FIG. 8 is a schematic diagram of a control system 800, which may be utilized with a surgical visualization system 700. The depicted control system 800 includes a control circuit 801 in signal communication with a memory 802. The memory 802 stores instructions executable by the control circuit 801 to determine and/or recognize critical structures (e.g., critical structures 701a, 701b depicted in FIG. 7), determine and/or compute one or more distances and/or three-dimensional digital representations, and to communicate certain information to one or more clinicians. For example, a memory 802 stores surface mapping logic 803, imaging logic 804, tissue identification logic 805), or distance determining logic 806 or any combinations of logic 803, 804, 805, 806. The control system 800 also includes an imaging system 807 having one or more cameras 808 (like the imaging device 707 depicted in FIG. 7), one or more displays 809, one or more controls 810 or any combinations of these elements. The one or more cameras 808 may include one or more image sensors 811 to receive signals from various light sources emitting light at various visible and invisible spectra (e.g., visible light, spectral imagers, three-dimensional lens, among others). The display 809 may include one or more screens or monitors for depicting real, virtual, and/or virtually-augmented images and/or information to one or more clinicians.

In various aspects, a main component of a camera 808 includes an image sensor 811. An image sensor 811 may include a Charge-Coupled Device (CCD) sensor, a Complementary Metal Oxide Semiconductor (CMOS) sensor, a short-wave infrared (SWIR) sensor, a hybrid CCD/CMOS architecture (sCMOS) sensor, and/or any other suitable kind(s) of technology. An image sensor 811 may also include any suitable number of chips.

The depicted control system 800 also includes a spectral light source 812 and a structured light source 813. In certain instances, a single source may be pulsed to emit wavelengths of light in the spectral light source 812 range and wavelengths of light in the structured light source 813 range. Alternatively, a single light source may be pulsed to provide light in the invisible spectrum (e.g., infrared spectral light) and wavelengths of light on the visible spectrum. A spectral light source 812 may include a hyperspectral light source, a multispectral light source, a fluorescence excitation light source, and/or a selective spectral light source, for example. In various instances, tissue identification logic 805 may identify critical structure(s) via data from a spectral light source 812 received by the image sensor 811 portion of a camera 808. Surface mapping logic 803 may determine the surface contours of the visible tissue based on reflected structured light. With time-of-flight measurements, distance determining logic 806 may determine one or more distance(s) to the visible tissue and/or critical structure(s) 701a, 701b. One or more outputs from surface mapping logic 803, tissue identification logic 805, and distance determining logic 806, may be provided to imaging logic 804, and combined, blended, and/or overlaid to be conveyed to a clinician via the display 809 of the imaging system 807.

III. EXEMPLARY COMBINATION

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical visualization system comprising: (a) a stereo camera comprising a first image sensor and a second image sensor; and (b) a processor configured to obtain calibration data for the stereo camera and, during a surgical procedure, perform a set of three dimensional position determination tasks comprising: (i) capturing a first image of a surgical site from the first image sensor and a second image of the surgical site from the second image sensor; (ii) using the calibration data, deriving a first corrected image based on the first image, and a second corrected image based on the second image; (iii) determining an offset by performing one or more steps comprising comparing the first corrected image and the second corrected image; (iv) determining, based on the offset, whether the stereo camera requires recalibration; (v) in the event that the stereo camera is determined to require recalibration, performing at least one recalibration action; and (vi) determining, for each of one or more points in the surgical site, a three dimensional position of that point based on the calibration data and data from the first and second image sensors.

Example 2

The system of example 1, wherein (a) the processor is configured perform a set of calibration image set creation tasks comprising capturing a first set of images depicting a known object in the surgical site using the first image sensor, and a second set of images depicting the known object in the surgical site using the second image sensor, wherein each image from the first set of images has a corresponding image from the second set of images captured simultaneously with that image from the first set of images; and (b) the at least one recalibration action comprises updating the calibration data based on the known object in the surgical site from the first set of images and the known object in the surgical site from the second set of images.

Example 3

The system of example 2, wherein (a) the known object in the surgical site is a surgical tool; (b) the set of calibration image set creation tasks is comprised by the at least one recalibration action; and (c) the set of calibration image set creation tasks comprises presenting instructions to a user to move the surgical tool in the surgical site.

Example 4

The system of example 2, wherein: (a) the set of calibration image set creation tasks is comprised by the at least one recalibration action; and (b) the set of calibration image set creation tasks comprises presenting instructions to a user to obtain different views of the known object by moving the stereo camera.

Example 5

The system of example 2, wherein: (a) the surgical visualization system comprises a memory; (b) the processor is configured to repeatedly perform the set of three dimensional position determination tasks during the surgical procedure; (c) the processor is configured to capture the first set of images depicting the known object in the surgical site by, each time the task of capturing the first image of the surgical site from the first image sensor and the second image of the surgical site from the second image sensor is performed, storing the first image of the surgical from the first image sensor and the second image of the surgical site from the second image sensor in a buffer in the memory; and (d) the first set of images depicting the known object in the surgical site comprises images from the first image sensor in the buffer, and the second set of images depicting the known object in the surgical site comprises images from the second image sensor in the buffer.

Example 6

The system of example 1, wherein the at least one recalibration action comprises providing a recalibration notice to a user.

Example 7

The system of example 1, wherein (a) the first corrected image and the second corrected image each depict a surgical tool in the surgical site; and (b) determining the offset by performing one or more steps comprising comparing the first corrected image and the second corrected image comprises comparing the depiction of the surgical tool in the first corrected image and the second corrected image.

Example 8

The system of example 7, wherein: (a) The surgical tool comprises a feature; and (b) determining the offset comprises: (i) identifying the feature in the depiction of the surgical tool in the first corrected image and the depiction of the surgical tool in the second corrected image; and (ii) determining a distance between the feature in the depiction of the surgical tool in the first corrected image and the feature in the depiction of the surgical tool in the second corrected image in a direction perpendicular to a line segment connecting corresponding points in the first image sensor and the second image sensor.

Example 9

The system of example 8, wherein: (a) the feature comprised by the surgical tool is a distal tip of the surgical tool; and (b) the line segment connecting corresponding points in the first image sensor connects a center of the first image sensor and a center of the second image sensor.

Example 10

The system of example 8, wherein determining, based on the offset, whether the stereo camera requires recalibration comprises: (a) converting the distance between the feature in the depiction of the surgical tool in the first corrected image and the feature in the depiction of the surgical tool in the second corrected image from pixels to millimeters based on a known dimension of the surgical tool; and (b) comparing the distance of in millimeters to a threshold associated with the surgical procedure.

Example 11

The system of example 1, wherein (a) the at least one recalibration action comprises updating the calibration data; and (b) determining, for each of one or more points in the surgical site, the three dimensional position of that point based on the calibration data and data from the first and second image sensors comprises: (i) in the event that the stereo camera is determined not to require recalibration, determining, for each of one or more points in the surgical site, the three dimensional position of that point based on the first corrected image and the second corrected image; and (ii) in the event that the stereo camera is determined to require recalibration, determining, for each of one or more points in the surgical site, the three dimensional position of that point, based on a first new corrected image and a second new corrected image, wherein the first new corrected image and the second new corrected image are generated using the calibration data after updating the calibration data by performing the at least one recalibration action.

Example 12

The system of example 1, wherein determining, for each of one or more points in the surgical site, the three dimensional position of that point is comprised by generating a three dimensional reconstruction of the surgical scene.

Example 13

The system of example 1, wherein determining, for each of one or more points in the surgical site, the three dimensional position of that point comprises triangulating the three dimensional position of each of the one or more points.

Example 14

A method of recalibrating a stereo camera during a surgical procedure, the method comprising performing a set of three dimensional position determination tasks comprising: (a) capturing a first image of a surgical site from the first image sensor comprised by the stereo camera and a second image of the surgical site from a second image sensor comprised by the stereo camera; (b) using calibration data for the stereo camera, deriving a first corrected image based on the first image, and a second corrected image based on the second image; (c) determining an offset by performing one or more steps comprising comparing the first corrected image and the second corrected image; (d) determining, based on the offset, whether the stereo camera requires recalibration; and (e) based on determining that the stereo camera requires recalibration, performing at least one recalibration action.

Example 15

The method of example 14, wherein: (a) the method comprises performing a set of calibration image set creation tasks comprising capturing a first set of images depicting a known object in the surgical site using the first image sensor, and a second set of images depicting the known object in the surgical site using the second image sensor, wherein each image from the first set of images has a corresponding image from the second set of images captured simultaneously with that image from the first set of images; and (b) the at least one recalibration action comprises updating the calibration data for the stereo camera based on the known object in the surgical site from the first set of images and the known object in the surgical site from the second set of images.

Example 16

The method of example 15, wherein: (a) the known object in the surgical site is a surgical tool; (b) the set of calibration image set creation tasks is comprised by the at least one recalibration action; and (c) the set of calibration image set creation tasks comprises presenting instructions to a user of a surgical visualization system to move the surgical tool in the surgical site.

Example 17

The method of example 15, wherein: (a) the method comprising repeatedly performing the set of three dimensional position determination tasks during the surgical procedure; (b) capturing the first set of images depicting the known object in the surgical site is performed by, each time the task of capturing the first image of the surgical site from the first image sensor and the second image of the surgical site from the second image sensor is performed, storing the first image of the surgical from the first image sensor and the second image of the surgical site from the second image sensor in a buffer in a memory comprised by a surgical visualization system; and (c) the first set of images depicting the known object in the surgical site comprises images from the first image sensor in the buffer, and the second set of images depicting the known object in the surgical site comprises images from the second image sensor in the buffer.

Example 18

The method of example 114, wherein: (a) the first corrected image and the second corrected image each depict a surgical tool in the surgical site; (b) the surgical tool comprises a features; and (c) determining the offset by performing one or more steps comprising comparing the first corrected image and the second corrected image comprises: (i) identifying the feature in the depiction of the surgical tool in the first corrected image and the depiction of the surgical tool in the second corrected image; and (ii) determining a distance between the feature in the depiction of the surgical tool in the first corrected image and the feature in the depiction of the surgical tool in the second corrected image in a direction perpendicular to a line segment connecting corresponding points in the first image sensor and the second image sensor.

Example 19

The method of example 18, wherein determining, based on the offset, whether the stereo capture requires recalibration comprises: (a) converting the distance between the feature in the depiction of the surgical tool in the first corrected image and the feature in the depiction of the surgical tool in the second corrected image from pixels to millimeters based on a known dimension of the surgical tool; and (b) comparing the distance of in millimeters to a threshold associated with the surgical procedure.

Example 20

A non-transitory computer readable medium storing instructions operable to, when executed by a processor, cause a surgical visualization system to perform a set of three dimensional position determination tasks comprising: (a) capturing a first image of a surgical site from a first image sensor comprised by a stereo camera and a second image of the surgical site from a second image sensor comprised by the stereo camera; (b) using calibration data for the stereo camera, deriving a first corrected image based on the first image, and a second corrected image based on the second image; (c) determining an offset by performing one or more steps comprising comparing the first corrected image and the second corrected image; (d) determining, based on the offset, whether the stereo camera requires recalibration; (e) in the event that the stereo camera is determined to require recalibration, performing at least one recalibration action; and (f) determining, for each of one or more points in the surgical site, a three dimensional position of that point based on the calibration data for the stereo camera and data from the first and second image sensors.

Example 21

The non-transitory computer readable medium of example 20, wherein: (a) the instructions are operable to, when executed by the processor, cause the processor to perform a set of calibration image set creation tasks comprising capturing a first set of images depicting a known object in the surgical site using the first image sensor, and a second set of images depicting the known object in the surgical site using the second image sensor, wherein each image from the first set of images has a corresponding image from the second set of images captured simultaneously with that image from the first set of images; and (b) the at least one recalibration action comprises updating the calibration data for the stereo camera based on the known object in the surgical site from the first set of images and the known object in the surgical site from the second set of images.

Example 22

The non-transitory computer readable medium of example 20, wherein: (a) the first corrected image and the second corrected image each depict a surgical tool in the surgical site; (b) the surgical tool comprises a features; and (c) determining the offset by performing one or more steps comprising comparing the first corrected image and the second corrected image comprises: (i) identifying the feature in the depiction of the surgical tool in the first corrected image and the depiction of the surgical tool in the second corrected image; and (ii) determining a distance between the feature in the depiction of the surgical tool in the first corrected image and the feature in the depiction of the surgical tool in the second corrected image in a direction perpendicular to a line segment connecting corresponding points in the first image sensor and the second image sensor.

Example 23

The non-transitory computer readable medium of example 20, wherein determining, for each of one or more points in the surgical site, the three dimensional position of that point is comprised by generating a three dimensional reconstruction of the surgical scene.

Example 24

The non-transitory computer readable medium of example 20, wherein determining, for each of one or more points in the surgical site, the three dimensional position of that point comprises triangulating the three dimensional position of each of the one or more points.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they may be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that may penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical visualization system comprising:
   (a) a stereo camera comprising a first image sensor and a second image sensor; and
   (b) a processor configured to obtain calibration data for the stereo camera and, during a surgical procedure, perform a set of three dimensional position determination tasks comprising:
      (i) capturing a first image of a surgical site from the first image sensor and a second image of the surgical site from the second image sensor;
      (ii) using the calibration data, deriving a first corrected image based on the first image, and a second corrected image based on the second image;
      (iii) determining an offset by performing one or more steps comprising comparing the first corrected image and the second corrected image;
      (iv) determining, based on the offset, whether the stereo camera requires recalibration;
      (v) in the event that the stereo camera is determined to require recalibration, performing at least one recalibration action; and
      (vi) determining, for each of one or more points in the surgical site, a three dimensional position of that point based on the calibration data and data from the first and second image sensors.

2. The system of claim 1, wherein:
   (a) the processor is configured perform a set of calibration image set creation tasks comprising capturing a first set of images depicting a known object in the surgical site using the first image sensor, and a second set of images depicting the known object in the surgical site using the second image sensor, wherein each image from the first set of images has a corresponding image from the second set of images captured simultaneously with that image from the first set of images; and
   (b) the at least one recalibration action comprises updating the calibration data based on the known object in the surgical site from the first set of images and the known object in the surgical site from the second set of images.

3. The system of claim 2, wherein:
   (a) the known object in the surgical site is a surgical tool;
   (b) the set of calibration image set creation tasks is comprised by the at least one recalibration action; and
   (c) the set of calibration image set creation tasks comprises presenting instructions to a user to move the surgical tool in the surgical site.

4. The system of claim 2, wherein:
   (a) the set of calibration image set creation tasks is comprised by the at least one recalibration action; and
   (b) the set of calibration image set creation tasks comprises presenting instructions to a user to obtain different views of the known object by moving the stereo camera.

5. The system of claim 2, wherein:
   (a) the surgical visualization system comprises a memory;
   (b) the processor is configured to repeatedly perform the set of three dimensional position determination tasks during the surgical procedure;
   (c) the processor is configured to capture the first set of images depicting the known object in the surgical site by, each time the task of capturing the first image of the surgical site from the first image sensor and the second image of the surgical site from the second image sensor is performed, storing the first image of the surgical from the first image sensor and the second image of the surgical site from the second image sensor in a buffer in the memory; and
   (d) the first set of images depicting the known object in the surgical site comprises images from the first image sensor in the buffer, and the second set of images depicting the known object in the surgical site comprises images from the second image sensor in the buffer.

6. The system of claim 1, wherein:
(a) the first corrected image and the second corrected image each depict a surgical tool in the surgical site; and
(b) determining the offset by performing one or more steps comprising comparing the first corrected image and the second corrected image comprises comparing the depiction of the surgical tool in the first corrected image and the second corrected image.

7. The system of claim 6, wherein:
(a) The surgical tool comprises a feature; and
(b) determining the offset comprises:
 (i) identifying the feature in the depiction of the surgical tool in the first corrected image and the depiction of the surgical tool in the second corrected image; and
 (ii) determining a distance between the feature in the depiction of the surgical tool in the first corrected image and the feature in the depiction of the surgical tool in the second corrected image in a direction perpendicular to a line segment connecting corresponding points in the first image sensor and the second image sensor.

8. The system of claim 7, wherein:
(a) the feature comprised by the surgical tool is a distal tip of the surgical tool; and
(b) the line segment connecting corresponding points in the first image sensor connects a center of the first image sensor and a center of the second image sensor.

9. The system of claim 7, wherein determining, based on the offset, whether the stereo camera requires recalibration comprises:
(a) converting the distance between the feature in the depiction of the surgical tool in the first corrected image and the feature in the depiction of the surgical tool in the second corrected image from pixels to millimeters based on a known dimension of the surgical tool; and
(b) comparing the distance of in millimeters to a threshold associated with the surgical procedure.

10. The system of claim 7, wherein:
(a) the first corrected image is a view of the surgical tool from the first image sensor; and
(b) the second corrected image is a view of the surgical tool from the second image sensor.

11. The system of claim 1, wherein:
(a) the at least one recalibration action comprises updating the calibration data; and
(b) determining, for each of one or more points in the surgical site, the three dimensional position of that point based on the calibration data and data from the first and second image sensors comprises:
 (i) in the event that the stereo camera is determined not to require recalibration, determining, for each of one or more points in the surgical site, the three dimensional position of that point based on the first corrected image and the second corrected image; and
 (ii) in the event that the stereo camera is determined to require recalibration, determining, for each of one or more points in the surgical site, the three dimensional position of that point, based on a first new corrected image and a second new corrected image, wherein the first new corrected image and the second new corrected image are generated using the calibration data after updating the calibration data by performing the at least one recalibration action.

12. A method of recalibrating a stereo camera during a surgical procedure, the method comprising performing a set of three dimensional position determination tasks comprising:
(a) capturing a first image of a surgical site from the first image sensor comprised by the stereo camera and a second image of the surgical site from a second image sensor comprised by the stereo camera;
(b) using calibration data for the stereo camera, deriving a first corrected image based on the first image, and a second corrected image based on the second image;
(c) determining an offset by performing one or more steps comprising comparing the first corrected image and the second corrected image;
(d) determining, based on the offset, whether the stereo camera requires recalibration; and
(e) based on determining that the stereo camera requires recalibration, performing at least one recalibration action.

13. The method of claim 12, wherein:
(a) the method comprises performing a set of calibration image set creation tasks comprising capturing a first set of images depicting a known object in the surgical site using the first image sensor, and a second set of images depicting the known object in the surgical site using the second image sensor, wherein each image from the first set of images has a corresponding image from the second set of images captured simultaneously with that image from the first set of images; and
(b) the at least one recalibration action comprises updating the calibration data for the stereo camera based on the known object in the surgical site from the first set of images and the known object in the surgical site from the second set of images.

14. The method of claim 13, wherein:
(a) the known object in the surgical site is a surgical tool;
(b) the set of calibration image set creation tasks is comprised by the at least one recalibration action; and
(c) the set of calibration image set creation tasks comprises presenting instructions to a user of a surgical visualization system to move the surgical tool in the surgical site.

15. The method of claim 13, wherein:
(a) the method comprising repeatedly performing the set of three dimensional position determination tasks during the surgical procedure;
(b) capturing the first set of images depicting the known object in the surgical site is performed by, each time the task of capturing the first image of the surgical site from the first image sensor and the second image of the surgical site from the second image sensor is performed, storing the first image of the surgical from the first image sensor and the second image of the surgical site from the second image sensor in a buffer in a memory comprised by a surgical visualization system; and
(c) the first set of images depicting the known object in the surgical site comprises images from the first image sensor in the buffer, and the second set of images depicting the known object in the surgical site comprises images from the second image sensor in the buffer.

16. The method of claim 12, wherein:
(a) the first corrected image and the second corrected image each depict a surgical tool in the surgical site;

(b) the surgical tool comprises a features; and (c) determining the offset by performing one or more steps comprising comparing the first corrected image and the second corrected image comprises:
 (i) identifying the feature in the depiction of the surgical tool in the first corrected image and the depiction of the surgical tool in the second corrected image; and
 (ii) determining a distance between the feature in the depiction of the surgical tool in the first corrected image and the feature in the depiction of the surgical tool in the second corrected image in a direction perpendicular to a line segment connecting corresponding points in the first image sensor and the second image sensor.

17. The method of claim 16, wherein determining, based on the offset, whether the stereo capture requires recalibration comprises:
 (a) converting the distance between the feature in the depiction of the surgical tool in the first corrected image and the feature in the depiction of the surgical tool in the second corrected image from pixels to millimeters based on a known dimension of the surgical tool; and
 (b) comparing the distance of in millimeters to a threshold associated with the surgical procedure.

18. A non-transitory computer readable medium storing instructions operable to, when executed by a processor, cause a surgical visualization system to perform a set of three dimensional position determination tasks comprising:
 (a) capturing a first image of a surgical site from a first image sensor comprised by a stereo camera and a second image of the surgical site from a second image sensor comprised by the stereo camera;
 (b) using calibration data for the stereo camera, deriving a first corrected image based on the first image, and a second corrected image based on the second image;
 (c) determining an offset by performing one or more steps comprising comparing the first corrected image and the second corrected image;
 (d) determining, based on the offset, whether the stereo camera requires recalibration;
 (e) in the event that the stereo camera is determined to require recalibration, performing at least one recalibration action; and
 (f) determining, for each of one or more points in the surgical site, a three dimensional position of that point based on the calibration data for the stereo camera and data from the first and second image sensors.

19. The non-transitory computer readable medium of claim 18, wherein:
 (a) the instructions are operable to, when executed by the processor, cause the processor to perform a set of calibration image set creation tasks comprising capturing a first set of images depicting a known object in the surgical site using the first image sensor, and a second set of images depicting the known object in the surgical site using the second image sensor, wherein each image from the first set of images has a corresponding image from the second set of images captured simultaneously with that image from the first set of images; and
 (b) the at least one recalibration action comprises updating the calibration data for the stereo camera based on the known object in the surgical site from the first set of images and the known object in the surgical site from the second set of images.

20. The non-transitory computer readable medium of claim 18, wherein:
 (a) the first corrected image and the second corrected image each depict a surgical tool in the surgical site;
 (b) the surgical tool comprises a features; and
 (c) determining the offset by performing one or more steps comprising comparing the first corrected image and the second corrected image comprises:
  (i) identifying the feature in the depiction of the surgical tool in the first corrected image and the depiction of the surgical tool in the second corrected image; and
  (ii) determining a distance between the feature in the depiction of the surgical tool in the first corrected image and the feature in the depiction of the surgical tool in the second corrected image in a direction perpendicular to a line segment connecting corresponding points in the first image sensor and the second image sensor.

* * * * *